(12) United States Patent
Swackhamer et al.

(10) Patent No.: US 10,092,764 B2
(45) Date of Patent: Oct. 9, 2018

(54) IMPLANTABLE MEDICAL DEVICE WITH MODIFIED SURFACE TEXTURE

(71) Applicant: Cardiac Pacemakers, Inc., St. Paul, MN (US)

(72) Inventors: Bryan J. Swackhamer, Shoreview, MN (US); Brian L. Schmidt, White Bear Lake, MN (US)

(73) Assignee: CARDIAC PACEMAKERS, INC., St. Paul, MN (US)

( * ) Notice: Subject to any disclaimer, the term of this patent is extended or adjusted under 35 U.S.C. 154(b) by 147 days.

(21) Appl. No.: 15/241,878

(22) Filed: Aug. 19, 2016

(65) Prior Publication Data

US 2017/0050028 A1    Feb. 23, 2017

Related U.S. Application Data

(60) Provisional application No. 62/207,738, filed on Aug. 20, 2015.

(51) Int. Cl.
| | |
|---|---|
| *A61N 1/37* | (2006.01) |
| *A61N 1/375* | (2006.01) |
| *A61N 1/372* | (2006.01) |
| *A61N 1/05* | (2006.01) |
| *A61N 1/362* | (2006.01) |

(52) U.S. Cl.
CPC ............. *A61N 1/375* (2013.01); *A61N 1/057* (2013.01); *A61N 1/362* (2013.01); *A61N 1/3756* (2013.01); *A61N 1/37205* (2013.01); *A61N 2001/0578* (2013.01)

(58) Field of Classification Search
CPC ........ A61N 1/375; A61N 1/057; A61N 1/362; A61N 1/37205; A61N 1/3756; A61N 2001/0578
See application file for complete search history.

(56) References Cited

U.S. PATENT DOCUMENTS

| | | |
|---|---|---|
| 5,755,762 A | 5/1998 | Bush |
| 6,168,633 B1 | 1/2001 | Itzhak et al. |
| (Continued) | | |

FOREIGN PATENT DOCUMENTS

WO    2012051235 A1    4/2012

OTHER PUBLICATIONS

International Search Report and Written Opinion for Application No. PCT/US2016/047802 13 pages, dated Feb. 23, 2017.

*Primary Examiner* — Paula J Stice
(74) *Attorney, Agent, or Firm* — Seager, Tufte & Wickhem LLP

(57) ABSTRACT

An implantable medical device has a housing with a fixation element disposed adjacent a first end of the housing and a retrieval element disposed adjacent a second end of the housing. An outer housing surface includes a first region having a first surface texture with a first average surface roughness and a second region having a second surface texture with a second average surface roughness that is different from the first average surface roughness. An insulative layer includes a first region overlying the first surface texture and a second region overlying the second surface texture, wherein an outer surface of the insulative layer emulates the first surface texture in the first region of the insulative layer and emulates the second surface texture in the second region of the insulative layer.

7 Claims, 9 Drawing Sheets

(56) References Cited

U.S. PATENT DOCUMENTS

| | | | |
|---|---|---|---|
| 6,549,811 B2 | 4/2003 | Stewart et al. | |
| 7,329,366 B1 | 2/2008 | Gale et al. | |
| 7,410,497 B2 | 8/2008 | Hastings et al. | |
| 7,499,757 B2 * | 3/2009 | Coe | A61B 17/0469 607/120 |
| 7,650,193 B2 | 1/2010 | Aron et al. | |
| 7,967,998 B2 | 6/2011 | Gale et al. | |
| 8,311,606 B2 | 11/2012 | Jiang et al. | |
| 8,346,374 B2 | 1/2013 | Foster et al. | |
| 8,535,704 B2 | 9/2013 | Yang | |
| 8,903,511 B2 | 12/2014 | Aron et al. | |
| 9,017,489 B2 | 4/2015 | Rokicki | |
| 2003/0220677 A1 | 11/2003 | Doan et al. | |
| 2008/0243243 A1 | 10/2008 | Williams et al. | |
| 2009/0062895 A1 * | 3/2009 | Stahmann | A61N 1/05 607/122 |
| 2009/0204170 A1 * | 8/2009 | Hastings | A61N 1/0565 607/33 |
| 2012/0116489 A1 * | 5/2012 | Khairkhahan | A61N 1/375 607/127 |
| 2015/0044421 A1 | 2/2015 | Hassan et al. | |

\* cited by examiner

IMPLANTABLE MEDICAL DEVICE WITH MODIFIED SURFACE TEXTURE

CROSS REFERENCE TO RELATED APPLICATIONS

This application claims the benefit of U.S. Provisional Patent Application Ser. No. 62/207,738 filed on Aug. 20, 2015, the disclosure of which is incorporated herein by reference.

TECHNICAL FIELD

The present disclosure generally relates to implantable medical devices and more particularly to implantable cardiac pacemakers.

BACKGROUND

Heart conditions can lead to rapid, irregular, and/or inefficient heart contractions. This can reduce the cardiac output of the heart, cause damage to the heart, and even lead to death. To help alleviate some of these conditions, pacemakers, defibrillators and/or other cardiac devices are often implanted in the patient's body. Such implantable cardiac devices can provide electrical stimulation to the heart to help the heart operate in a more normal, efficient and/or safe manner. It is desirable for such implantable devices to remain in place once implanted. In some cases, it is desirable to remove, reposition and/or replace such implanted medical devices after implanted.

SUMMARY

The present disclosure generally relates to implantable medical devices and more particularly to implantable cardiac pacemakers. A first example implantable medical device may include a housing including a first end and a second end. A fixation element may be disposed adjacent the first end of the housing, and a retrieval element may be disposed adjacent the second end of the housing. The housing may include an outer housing surface that has a first region with a first surface texture having a first average surface roughness and a second region with a second surface texture having a second average surface roughness that is different from the first average surface roughness. An insulative layer may be disposed over the first surface texture and the second surface texture of the outer housing surface. The insulative layer may include a first region overlying the first surface texture and a second region overlying the second surface texture. An outer surface of the insulative layer may emulate the first surface texture in the first region of the insulative layer and may emulate the second surface texture in the second region of the insulative layer.

Alternatively or additionally to any of the embodiments above, the implantable medical device is a leadless cardiac pacemaker.

Alternatively or additionally to any of the embodiments above, the retrieval element is configured to be ensnared for subsequent removal of the implantable medical device.

Alternatively or additionally to any of the embodiments above, the first surface texture with the first average surface roughness represents a native surface texture of the material forming the outer housing surface.

Alternatively or additionally to any of the embodiments above, the second surface texture corresponds to a region of the outer housing surface that has been treated to make the second region of the outer housing surface smoother than the first region of the outer housing surface.

Alternatively or additionally to any of the embodiments above, the first region of the outer housing surface comprises two or more distinct areas having the first surface texture.

Alternatively or additionally to any of the embodiments above, the second region of the outer housing surface comprises two or more distinct areas having the second surface texture.

A second example implantable medical device may include:
a housing including a first end and a second end;
a fixation element disposed adjacent the first end of the housing;
a retrieval element disposed adjacent the second end of the housing;
the housing including an outer housing surface, the outer housing surface including a first surface region that is configured to promote endothelial cell growth and a second surface region that is configured to discourage endothelial cell growth;
an insulative layer disposed over the first surface region and the second surface region of the outer housing surface, the insulative layer including a first region emulating the first surface region and a second region emulating the second surface region.

Alternatively or additionally to the second example implantable medical device above, the first surface region that is configured to promote endothelial cell growth has a first average surface roughness value and the second surface region that is configured to discourage endothelial cell growth has a second average surface roughness value that is lower than the first average surface roughness value.

A third example implantable medical device may include:
a housing defining an outer housing surface;
the outer housing surface defining a first surface texture in a first region and a second surface texture in a second region, wherein the first surface texture is different from the second surface texture;
a conformal coating disposed over the first surface texture and the second surface texture, wherein an outer surface of the conformal coating emulates the first surface texture in the first region and emulates the second surface texture in the second region; and
the first surface texture and the second surface texture are configured to promote more endothelialization in the first region than in the second region.

Alternatively or additionally to the third example implantable medical device above, the first surface texture is uniform across the first region, and the second surface texture is uniform across the second region.

Alternatively or additionally to any of the embodiments above with respect to the third example implantable medical device, the first surface texture has a first average surface roughness and the second surface texture has a second average surface roughness.

Alternatively or additionally to any of the embodiments above with respect to the third example implantable medical device, the first average surface roughness has an amplitude and a frequency and the second average surface roughness has an amplitude and a frequency, wherein the amplitude of the first average surface roughness is larger than the amplitude of the second average surface roughness.

Alternatively or additionally to any of the embodiments above with respect to the third example implantable medical device, the frequency of the first average surface roughness is less than the frequency of the second average surface roughness.

Alternatively or additionally to any of the embodiments above with respect to the third example implantable medical device, the conformal coating comprises Parylene.

Alternatively or additionally to any of the embodiments above with respect to the third example implantable medical device, the outer housing surface comprises a metal.

Alternatively or additionally to any of the embodiments above with respect to the third example implantable medical device, the first surface texture is provided in the outer housing surface by a removal process that removes material from the outer housing surface.

Alternatively or additionally to any of the embodiments above with respect to the third example implantable medical device, the first surface texture is provided in the outer housing surface by an additive process that adds material to the outer housing surface.

Alternatively or additionally to any of the embodiments above with respect to the third example implantable medical device, the second surface texture is provided in the outer housing surface by polishing.

Alternatively or additionally to any of the embodiments above with respect to the third example implantable medical device, the second surface texture represents a native texture of the material forming the outer housing surface.

The above summary is not intended to describe each embodiment or every implementation of the present disclosure. Advantages and attainments, together with a more complete understanding of the disclosure, will become apparent and appreciated by referring to the following description and claims taken in conjunction with the accompanying drawings.

BRIEF DESCRIPTION OF THE DRAWINGS

The disclosure may be more completely understood in consideration of the following description of various illustrative embodiments in connection with the accompanying drawings, in which.

Figure 1:
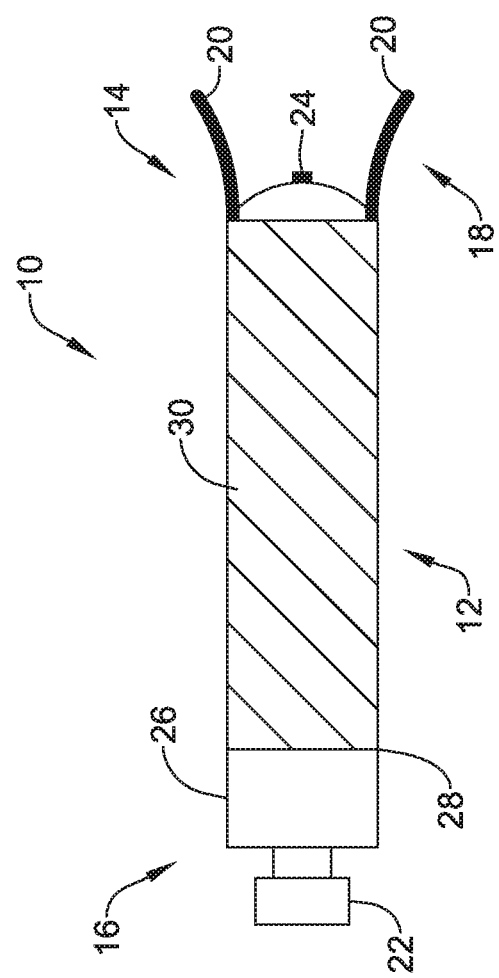
FIG. 1 is a schematic view of an illustrative leadless cardiac pacemaker (LCP) according to an example implantable medical device.

While the disclosure is amenable to various modifications and alternative forms, specifics thereof have been shown by way of example in the drawings and will be described in detail. It should be understood, however, that the intention is not to limit aspects of the disclosure to the particular illustrative embodiments described. On the contrary, the intention is to cover all modifications, equivalents, and alternatives falling within the spirit and scope of the disclosure.

DESCRIPTION

The following description should be read with reference to the drawings in which similar elements in different drawings are numbered the same. The description and the drawings, which are not necessarily to scale, depict illustrative embodiments and are not intended to limit the scope of the disclosure.

A normal, healthy heart induces contraction by conducting intrinsically generated electrical signals throughout the heart. These intrinsic signals cause the muscle cells or tissue of the heart to contract. This contraction forces blood out of and into the heart, providing circulation of the blood throughout the rest of the body. Many patients suffer from cardiac conditions that affect this contractility of their hearts. For example, some hearts may develop diseased tissues that no longer generate or conduct intrinsic electrical signals. In some examples, diseased cardiac tissues conduct electrical signals at differing rates, thereby causing an unsynchronized and/or inefficient contraction of the heart. In other examples, a heart may generate intrinsic signals at such a low rate that the heart rate becomes dangerously low. In still other examples, a heart may generate electrical signals at an unusually high rate. In some cases such an abnormality can develop into a fibrillation state, where the contraction of the patient's heart chambers are almost completely de-synchronized and the heart pumps very little to no blood. Implantable medical devices may be configured to determine occurrences of such cardiac abnormalities or arrhythmias and deliver one or more types of electrical stimulation therapy to the patient's hearts to help terminate and/or alleviate such cardiac conditions.

FIG. 1 is a schematic view of an illustrative leadless cardiac pacemaker (LCP) 10. While an LCP is shown as an example of an implantable medical device, it will be appreciated that the implantable medical device may be any suitable implantable device. For example, the implantable medical device may be an implantable cardiac monitor that is implanted on or in a patients' heart that monitors the patient's heart. One example implantable cardiac monitor may be similar to illustrative LCP 10 but may not have the capability to deliver therapy to the heart. Instead, the implantable cardiac monitor may simply monitor the heart function and communicate at least some of the monitored data to one or more remote devices such as an LCP 10, an external device such as a patient monitoring device, and/or any other suitable device or devices. In some cases, such an implantable cardiac monitor may itself perform some diagnostics based on the monitored data, and report alerts to one or more remote devices, but this is not required.

In any event, it is contemplated that the exemplary leadless cardiac pacemaker (LCP) 10 may be implanted into a patient and may operate to pace the patient's heart at a desired pacing rate in accordance with an appropriate therapy protocol (e.g. bradycardia therapy, cardiac resynchronization therapy (CRT), and/or the like). In some cases, the exemplary leadless cardiac pacemaker (LCP) 10 may help prevent, control, or terminate cardiac arrhythmias in patients, for example by appropriately employing one or more therapies (e.g. anti-tachycardia pacing (ATP) therapy, defibrillation pulses, and/or the like).

In the example shown in FIG. 1, the LCP 10 includes a housing 12 that houses internal components, which will be described further with respect to FIG. 9. The illustrative housing 12 includes a first end 14 and a second end 16. In some instances, the first end 14 may correspond to a distal end of the housing 12 and the second end 16 may correspond to a proximal end of the housing 12, but this is not required. In this instance, the term "distal" refers to the end of the housing 12 adjacent a fixation element 18, and the term "proximal" refers to the end of the housing 12 that is adjacent a retrieval element 22. As illustrated, the LCP 10 includes a fixation element 18 that is used to fix the LCP 10 to the heart tissue of a patient. A variety of different fixation elements are contemplated, including but not limited to one or more pins, staples, threads, screws, helices, tines, and/or the like. In the example shown, the fixation element 18 includes several tines 20. In some cases, the tines 20 are configured to curl back on themselves, in a fish hook manner, once implanted in cardiac tissue. In some cases, the LCP 10 may include a retrieval element 22, which may be used for retrieval of the LCP 10 after implantation. For example, in some cases, the retrieval element 22 may be ensnared using a retrieval snare (not shown).

In order to provide sensing and/or pacing capabilities, the LCP 10 may include one or more electrodes. In the example shown, the LCP 10 includes a distal electrode 24 and a proximal electrode 26. In other instances, the LCP 10 may include additional electrodes.

The housing 12 includes or otherwise defines an outer housing surface 28. In some cases, the housing 12 is formed of a metal, and thus is electrically conductive. An insulative layer 30 that is electrically insulating may be disposed over at least a portion of the outer housing surface 28. In some cases, one or more of the electrodes, such as the proximal electrode 26, may be defined by a region of the housing 12 that is exposed by a gap or void in the insulative layer 30.

It will be appreciated that the outer housing surface 28 may be considered as having a surface texture, with an average surface roughness. In some cases, the outer housing surface 28 may have a uniform surface texture, with a uniform average surface roughness. In some instances, as will be illustrated in subsequent drawings, the outer housing surface 28 may not have a uniform surface texture, but may instead have one or more areas with a first surface texture having a first average surface roughness and one or more areas with a second surface texture having a second average surface roughness that is different from the first average surface roughness. In other words, one or more areas of the outer housing surface 28 may be rougher than other areas of the outer housing surface. In some cases, one or more areas of the outer housing surface 28 may be smoother than other portions.

In some instances, the first surface texture may represent a native surface texture of the material forming the outer housing surface 28. In some cases, the first surface texture may represent an intentional roughening of the outer housing surface 28. In some cases, for example, the first surface texture may result from a removal process that removes material from the outer housing surface 28 or from an additive process that adds material to the outer housing surface 28. In some cases, the second surface texture may be the result of a surface treatment that renders portion(s) of the outer housing surface 28 smoother than the first surface texture. Optionally, the second surface texture may represent a native texture of the material forming the outer housing surface 28.

In some embodiments, the insulative layer 30 may include or otherwise be formed of a conformal coating that, once applied, emulates the texture of the underlying surface. For example, if a first portion of the underlying surface is smooth and a second portion of the underlying surface is rough, the insulative layer 30 may have a first region disposed over the first portion of the underlying surface having a relatively smooth outer surface (of the insulative layer 30), and a second region disposed over the second portion of the underlying surface and thus having a relatively rougher outer surface (of the insulative layer 30). In some cases, a degree of emulation may be defined in terms of how closely an outer surface of the conformal coating matches the texture of the underlying surface. For example, the outer surface of the conformal coating may be considered as emulating the texture of the underlying surface if the outer surface conformal coating has a surface roughness that is at least a 50 percent of the surface roughness of the underlying surface. Emulation may be defined, for example, as the outer surface conformal coating having a surface roughness that is at least a 60 percent, at least 70 percent, at least 80 percent, at least 90 percent, or at least 95 percent, of the surface roughness of the underlying surface.

The insulative layer 30 may be formed of any electrically insulating, conformal material. In some cases, the insulative layer 30 may include or otherwise be formed of a polymeric material such as Parylene. Parylene refers to a class of polymers known as xylylene polymers that are produced using a chemical vapor deposition (CVD) technique. In some embodiments, a chlorinated Parylene known as Parylene C may be used. In some embodiments, other materials such as insulative metal oxide such as titanium dioxide may be used. In some cases, an insulative metal oxide layer having sufficient thickness to be electrically insulative may be applied using physical vapor deposition. In some cases, the insulative layer 30 itself may also be chemically or mechanically abraded to form a rough texture and/or chemically or mechanically polished to form a smooth texture. This may be in addition to or, instead of, adjusting the texture of the outer housing surface 28.

In some cases, the degree of endothelialization, or the growth of endothelial and other cells on and about the LCP 10 may be influenced by controlling the texture of the outer housing surface 28 and thus the corresponding surface of the insulative layer 30. For example, an outer surface or portion thereof that is relatively rough may encourage endothelial cell growth while an outer surface or portion thereof that is relatively smooth may discourage endothelial cell growth. To illustrate, a surface having an average surface roughness that is less than about 10 micro inches Ra may encourage endothelial cell growth while a surface having an average surface roughness that is greater than about 30 micro inches Ra may discourage endothelial cell growth. It will be appreciated that these numbers are illustrative only.

In this, average surface roughness is defined in terms of $R_a$, which corresponds to an arithmetic average of the absolute heights of the surface features. $R_a$ is a one-dimensional parameter determined by the equation:

$$R_a = \frac{1}{n}\sum_{i=1}^{n}|y_i|,$$

where $y_i$ is an amplitude measurement of a single feature and n is the number of features. Surface roughness may be measured in a variety of ways. In some cases, surface roughness may be measured using a physical profilometer, which has a stylus that traces a line segment across a sample, or an optical profilometer, which uses interferometry to image an area of a sample.

In some cases, surface roughness may be defined in terms of amplitude and frequency, which of course provides an indication of how far apart the surface features are, such as peaks or troughs. Frequency may be defined, for example, as a mean spacing between surface features, meaning that a lower frequency means that surface features larger than a threshold are actually more common than a higher frequency. In some cases, a first average surface roughness has an amplitude and a frequency and a second average surface roughness has an amplitude and a frequency. In some instances, the amplitude of the first average surface roughness is larger than the amplitude of the second average surface roughness, and/or the frequency of the first average surface roughness is less than the frequency of the second average surface roughness.

FIGS. 2 through 8 provide illustrative but non-limiting examples of surface texture patterns that may be formed in or on the outer housing surface 28 in order to influence the resulting texture of the insulative layer 30 that is disposed over at least a portion of the outer housing surface 28 and thus influence an expected level of endothelial cell growth. For simplicity, the fixation element 18 is not shown in FIGS. 2-8. Likewise, the insulative layer 30 is not shown, although it will be appreciated that the insulative layer 30, when provided, may also emulate the underlying texture. It should be noted that the texture patterns shown in FIGS. 2 through 8 are intended to illustrate patterns in texturing, i.e., which areas are smooth and which areas are rough, rather than indicating actual texture. The actual texture, especially in rough area(s), may be regular or irregular, in a repeating or random pattern, may include defined shapes, etc.

As noted, the relative roughness may be useful in dictating portions of the outer housing surface 28 over which endothelial cell growth is encouraged or permitted and other portions of the outer housing surface 28 over which endothelial cell growth is discouraged. It will be appreciated that once the LCP 10 is implanted, endothelial cell growth will tend to begin at the first end 14, as it is this portion of the LCP 10 that is in direct contact with the cardiac tissue. In some cases, there can be a desire for at least a limited amount of endothelial cell growth at or near the first end 14 as the cellular growth can help to anchor the LCP 10 in position within the beating heart. However, there may be a desire to limit endothelial cell growth along other portions of the LCP 10 in order to, for example, facilitate possible subsequent removal of the LCP 10. A physician may wish to remove the LCP 10 if, for example, the battery within the LCP 10 becomes depleted. Alternatively, there may be a desire to remove and reposition the LCP 10 if a determination is made that its placement is sub-optimal.

In some cases, there may be a desire to limit endothelial cell growth along portions of the LCP 10 in order to keep an outer facing sensor 27 exposed to the blood. For example, an LCP 10 may include a pressure sensor, temperature sensor, flow sensor, gas sensor, and/or other sensor that, once the LCP 10 is implanted, is exposed to the blood surrounding the LCP 10. In some cases, endothelial cell growth over the sensing surface of the sensor 27 may reduce the effectiveness of the sensor.

Figure 2:
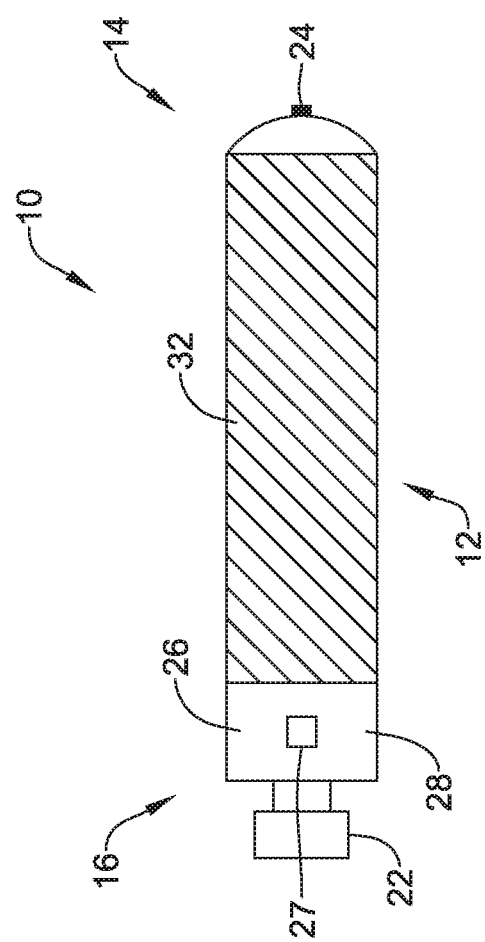
FIGS. 2 through 8 provide examples of surface texture patterning that may be employed with the leadless cardiac pacemaker (LCP) of FIG. 1.
Figure 3:
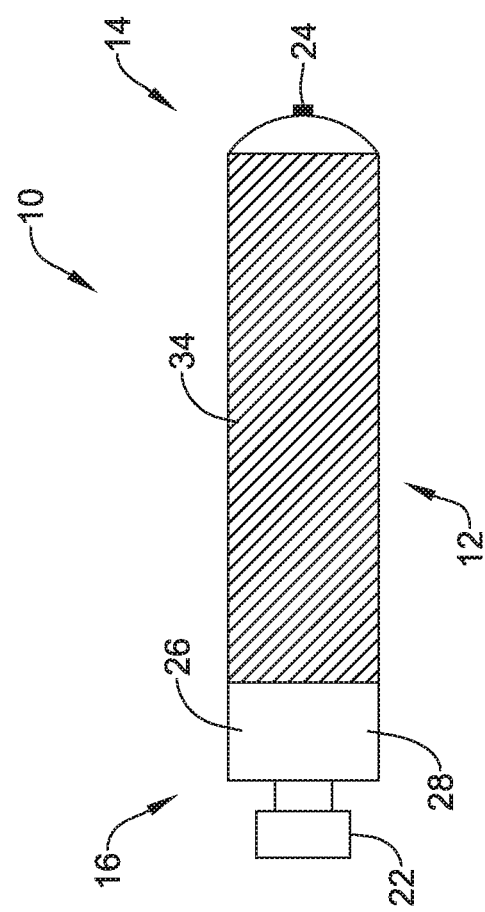

In FIG. 2, the outer housing surface 28 includes a rough portion 32 that covers most if not all of the outer housing surface 28. In this example, endothelialization will likely begin at or near the first end 14 of the LCP 10 and will progress proximally. A pattern such as this may be useful if assuring good anchoring is potentially more important than possible future removal. Conversely, in FIG. 3, the outer housing surface 28 includes a smooth portion 34 that covers most if not all of the outer housing surface 28. In this embodiment, endothelialization will likely be minimized along the length of the outer housing surface 28. This may be useful if assuring future removal is potentially more important than providing a secondary anchoring mechanism via endothelial cell growth.

Figure 4:
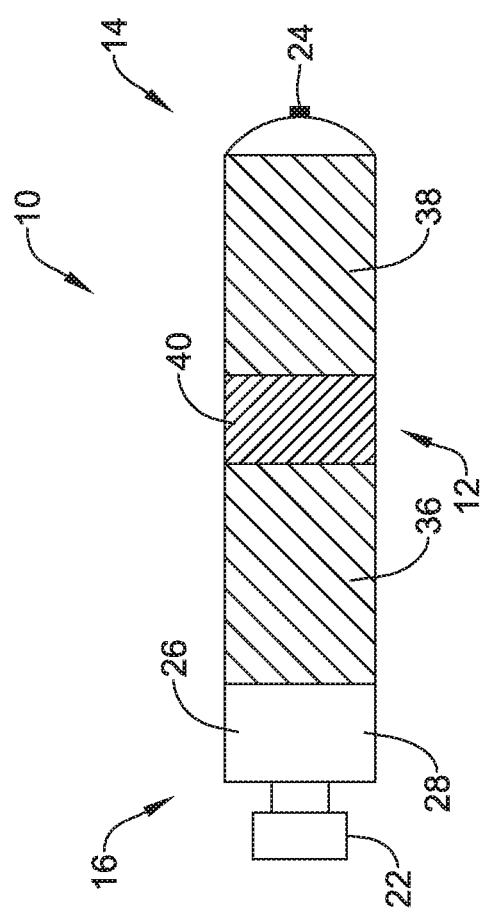
Figure 5:
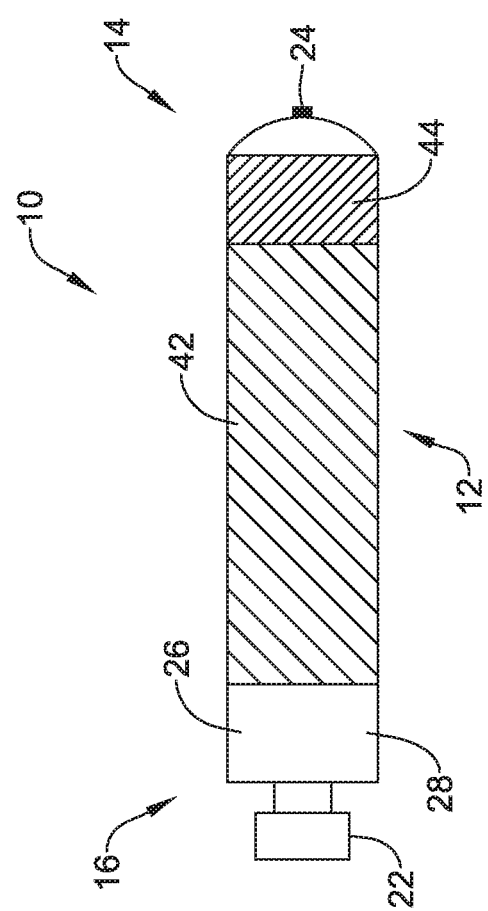
Figure 6:
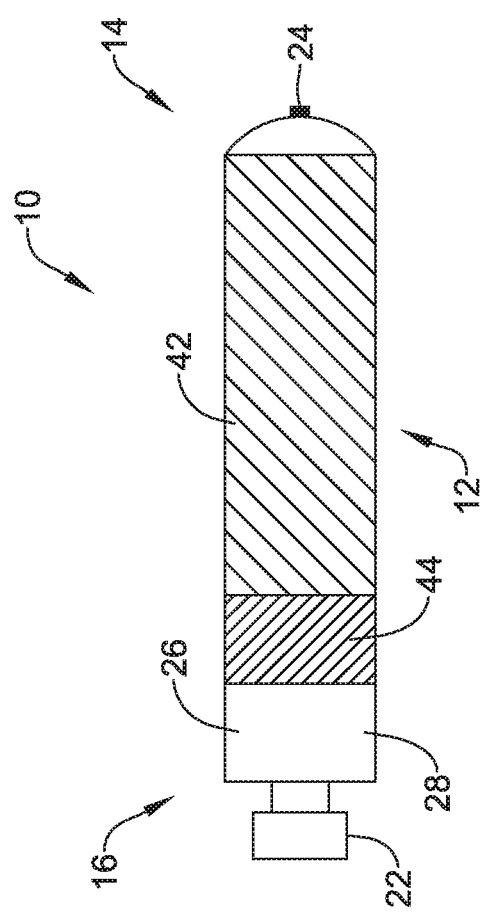

In FIG. 4, the outer housing surface 28 includes a first rough portion 36 and a second rough portion 38, separated by a smooth portion 40. In some instances, the first rough portion 36, the second rough portion 38, and the smooth portion 40 are all annular in shape, but this is not required. In this example, it will be appreciated that endothelial cell growth beginning at or near the first end 14 may continue proximally until encountering the smooth portion 40. In some instances, this pattern may provide a good combination of secondary anchoring via cell growth while affording good access to the retrieval element 22. FIG. 4 represents a midpoint between the embodiments shown in FIGS. 5 and 6. In FIG. 5, a rough portion 42 covers much of the outer housing surface 28, while a smooth portion 44 is disposed near the first end 14. This may minimize endothelial cell growth while not requiring additional processing of the outer housing surface 28. By contrast, in FIG. 6, the smooth portion 44 is disposed near the second end 16, which will afford substantial endothelial cell growth while helping to keep the retrieval element 22 accessible for possible ensnarement and removal. It will be appreciated that the relative widths of the rough portion 42 and the smooth portion 44 are illustrative only, and may be varied depending on the intended end use and environment of the LCP 10.

Figure 7:
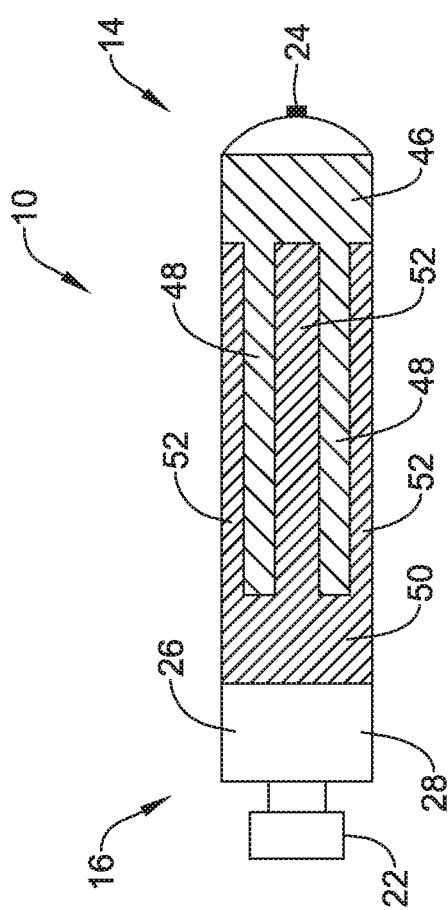

FIG. 7 is an example in which the outer housing surface 28 includes a rough portion 46 disposed near the first end 14, and including tendrils 48 extending towards the second end 16. The outer housing surface 28 includes a smooth portion 50 disposed near the second end 16, and including tendrils 52 extending towards the first end 14 and interwoven with the tendrils 48. In some cases, this example may provide a good combination of endothelial cell growth as a secondary anchoring mechanism while permitting subsequent retrieval if desired.

Figure 8:
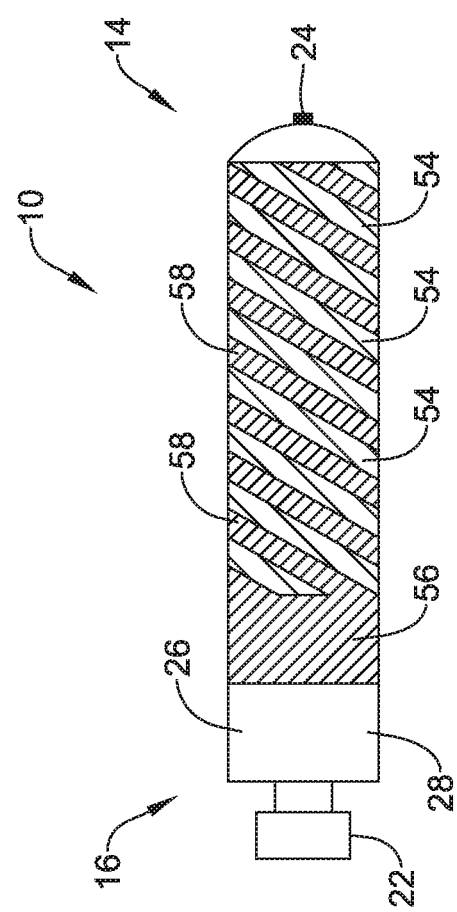

FIG. 8 illustrates an embodiment in which the outer housing surface 28 includes rough portions 54 woven between a smooth portion 56 that includes a spiral wound smooth portion 58. It will be appreciated that the dimensions and pitch of the smooth portion 56 may be varied, and that this design affords a longer linear section of endothelialization. In some cases, this design may also supplement a helical fixation element, if present, and the endothelialization may provide anti-rotation stability. In one example, the spiral wound smooth portion 58 may be formed in a helical direction that is opposite that of the helical fixation element.

Figure 9:
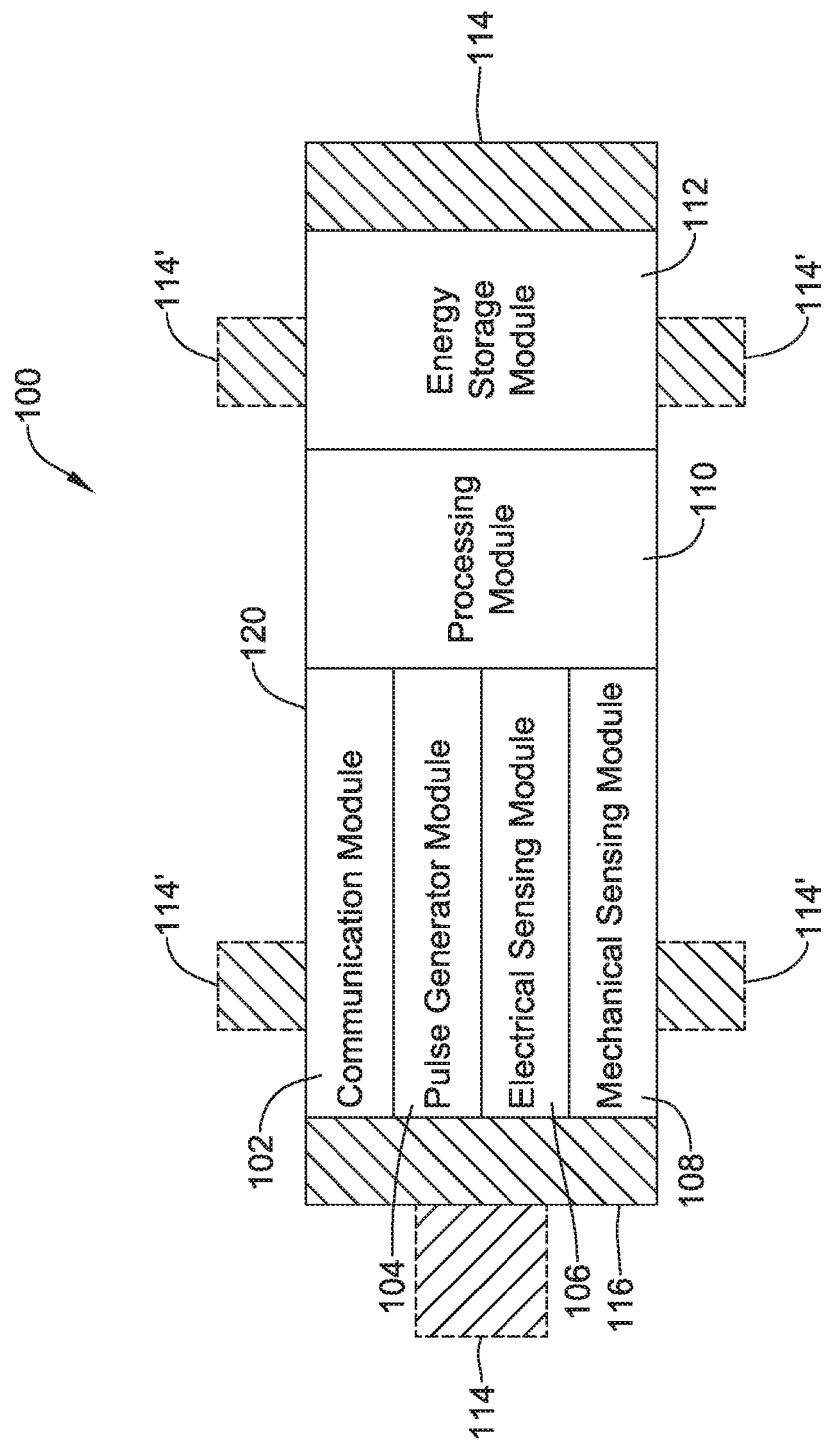
FIG. 9 is a schematic block diagram of an illustrative leadless cardiac pacemaker (LCP) according to an example of the present disclosure.

FIG. 9 illustrates some of the internal modules within an illustrative LCP 100. It will be appreciated that the LCP 100 may be considered as an example of the LCP 10 shown in FIGS. 1-8.

As can be seen, LCP 100 may be a compact device with all components housed within LCP 100 or directly on housing 120. In the example shown in FIG. 9, LCP 100 may include a communication module 102, a pulse generator module 104, an electrical sensing module 106, a mechanical sensing module 108, a processing module 110, a battery 112, and electrodes 114. The LCP 100 may include more or less modules, depending on the application.

The communication module 102 may be configured to communicate with devices such as sensors, other medical devices, and/or the like, that are located externally to LCP 100. Such devices may be located either external or internal to the patient's body. Irrespective of the location, external devices (i.e. external to the LCP 100 but not necessarily external to the patient's body) can communicate with the LCP 100 via the communication module 102 to accomplish one or more desired functions. For example, the LCP 100 may communicate information, such as sensed electrical signals, data, instructions, messages, etc., to an external medical device through the communication module 102.

The external medical device may use the communicated signals, data, instructions and/or messages to perform various functions, such as determining occurrences of arrhythmias, delivering electrical stimulation therapy, storing received data, displaying received data, and/or performing any other suitable function. The LCP 100 may additionally receive information such as signals, data, instructions and/or messages from the external medical device through the communication module 102, and the LCP 100 may use the received signals, data, instructions and/or messages to perform various functions, such as determining occurrences of arrhythmias, delivering electrical stimulation therapy, storing received data, and/or performing any other suitable function. The communication module 102 may be configured to use one or more methods for communicating with external devices. For example, the communication module 102 may communicate via radiofrequency (RF) signals, inductive coupling, optical signals, acoustic signals, conducted communication signals, and/or any other signals suitable for communication.

In the example shown in FIG. 9, the pulse generator module 104 may be electrically connected to the electrodes 114. In some examples, the LCP 100 may additionally include electrodes 114'. In such examples, the pulse generator 104 may also be electrically connected to the electrodes 114'. The pulse generator module 104 may be configured to generate electrical stimulation signals. For example, the pulse generator module 104 may generate electrical stimulation signals by using energy stored in the battery 112 within the LCP 100 and deliver the generated electrical stimulation signals via the electrodes 114 and/or 114'. Alternatively, or additionally, the pulse generator 104 may include one or more capacitors, and the pulse generator 104 may charge the one or more capacitors by drawing energy from the battery 112. The pulse generator 104 may then use the energy of the one or more capacitors to deliver the generated electrical stimulation signals via the electrodes 114 and/or 114'. In at least some examples, the pulse generator 104 of the LCP 100 may include switching circuitry to selectively connect one or more of the electrodes 114 and/or 114' to the pulse generator 104 in order to select which electrodes 114/114' (and/or other electrodes) the pulse generator 104 delivers the electrical stimulation therapy. The pulse generator module 104 may generate electrical stimulation signals with particular features or in particular sequences in order to provide one or multiple of a number of different stimulation therapies. For example, the pulse generator module 104 may be configured to generate electrical stimulation signals to provide electrical stimulation therapy to combat bradycardia, tachycardia, cardiac synchronization, bradycardia arrhythmias, tachycardia arrhythmias, fibrillation arrhythmias, cardiac synchronization arrhythmias and/or to produce any other suitable electrical stimulation therapy. Some more common electrical stimulation therapies include anti-tachycardia pacing (ATP) therapy, cardiac resynchronization therapy (CRT), and cardioversion/defibrillation therapy.

In some examples, the LCP 100 may not include a pulse generator 104. For example, the LCP 100 may be a diagnostic only device. In such examples, the LCP 100 may not deliver electrical stimulation therapy to a patient. Rather, the LCP 100 may collect data about cardiac electrical activity and/or physiological parameters of the patient and communicate such data and/or determinations to one or more other medical devices via the communication module 102.

In some examples, the LCP 100 may include an electrical sensing module 106, and in some cases, a mechanical sensing module 108. The electrical sensing module 106 may be configured to sense the cardiac electrical activity of the heart. For example, the electrical sensing module 106 may be connected to the electrodes 114/114', and the electrical sensing module 106 may be configured to receive cardiac electrical signals conducted through the electrodes 114/114'. The cardiac electrical signals may represent local information from the chamber in which the LCP 100 is implanted. For instance, if the LCP 100 is implanted within a ventricle of the heart, cardiac electrical signals sensed by the LCP 100 through the electrodes 114/114' may represent ventricular cardiac electrical signals. The mechanical sensing module 108 may include one or more sensors, such as an accelerometer, a blood pressure sensor, a heart sound sensor, a blood-oxygen sensor, a temperature sensor, a flow sensor and/or any other suitable sensors that are configured to measure one or more mechanical/chemical parameters of the patient. Both the electrical sensing module 106 and the mechanical sensing module 108 may be connected to a processing module 110, which may provide signals representative of the sensed mechanical parameters. Although described with respect to FIG. 9 as separate sensing modules, in some cases, the electrical sensing module 106 and the mechanical sensing module 108 may be combined into a single sensing module, as desired. In addition to, or instead of, the electrical sensing module 106 and/or the mechanical sensing module 108, the LCP 100 may include other types of sensing modules such as a magnetic sensing module, a chemical sensing module and/or a nuclear sensing module.

The electrodes 114/114' can be secured relative to the housing 120 but exposed to the tissue and/or blood surrounding the LCP 100. In some cases, the electrodes 114 may be generally disposed on either end of the LCP 100 and may be in electrical communication with one or more of the modules 102, 104, 106, 108, and 110. The electrodes 114/114' may be supported by the housing 120, although in some examples, the electrodes 114/114' may be connected to the housing 120 through short connecting wires such that the electrodes 114/114' are not directly secured relative to the housing 120. In examples where the LCP 100 includes one or more electrodes 114', electrodes 114' may in some cases be disposed on the sides of the LCP 100, which may increase the number of electrodes by which the LCP 100 may sense cardiac electrical activity, deliver electrical stimulation and/or communicate with an external medical device. The electrodes 114/114' can be made up of one or more biocompatible conductive materials such as various metals or alloys that are known to be safe for implantation within a human body. In some instances, the electrodes 114/114' connected to the LCP 100 may have an insulative portion that electrically isolates the electrodes 114/114' from adjacent electrodes, the housing 120, and/or other parts of the LCP 100.

The processing module 110 can be configured to control the operation of the LCP 100. For example, the processing module 110 may be configured to receive electrical signals from the electrical sensing module 106 and/or the mechanical sensing module 108. Based on the received signals, the processing module 110 may determine, for example, occurrences and, in some cases, types of arrhythmias. Based on any determined arrhythmias, the processing module 110 may control the pulse generator module 104 to generate electrical stimulation in accordance with one or more therapies to treat the determined arrhythmia(s). The processing module 110 may further receive information from the communication module 102. In some examples, the processing module 110 may use such received information to help determine whether an arrhythmia is occurring, determine a type of arrhythmia, and/or to take particular action in response to the information. The processing module 110 may additionally control the communication module 102 to send/receive information to/from other devices.

In some examples, the processing module 110 may include a pre-programmed chip, such as a very-large-scale integration (VLSI) chip and/or an application specific integrated circuit (ASIC). In such embodiments, the chip may be pre-programmed with control logic in order to control the operation of the LCP 100. By using a pre-programmed chip, the processing module 110 may use less power than other programmable circuits (e.g. general purpose programmable microprocessors) while still being able to maintain basic functionality, thereby potentially increasing the battery life of the LCP 100. In other examples, the processing module 110 may include a programmable microprocessor. Such a programmable microprocessor may allow a user to modify the control logic of the LCP 100 even after implantation, thereby allowing for greater flexibility of the LCP 100 than when using a pre-programmed ASIC. In some examples, the processing module 110 may further include a memory, and the processing module 110 may store information on and read information from the memory. In other examples, the LCP 100 may include a separate memory (not shown) that is in communication with the processing module 110, such that the processing module 110 may read and write information to and from the separate memory.

The battery 112 may provide power to the LCP 100 for its operations. In some examples, the battery 112 may be a non-rechargeable lithium-based battery. In other examples, a non-rechargeable battery may be made from other suitable materials, as desired. Because the LCP 100 is an implantable device, access to the LCP 100 may be limited after implantation. Accordingly, it is desirable to have sufficient battery capacity to deliver therapy over a period of treatment such as days, weeks, months, years or even decades. In some instances, the battery 112 may a rechargeable battery, which may help increase the useable lifespan of the LCP 100. In still other examples, battery 112 may be some other type of power source, as desired.

To implant the LCP 100 inside a patient's body, an operator (e.g., a physician, clinician, etc.), may fix the LCP 100 to the cardiac tissue of the patient's heart. To facilitate fixation, the LCP 100 may include one or more fixation elements 116. The fixation elements 116 may include any one of a number of fixation or anchoring mechanisms. For example, the fixation elements 116 may include one or more pins, staples, threads, screws, helices, tines, and/or the like. In some examples, although not shown, the fixation elements 116 may include threads on its external surface that may run along at least a partial length of the fixation elements 116. The threads may provide friction between the cardiac tissue and the fixation elements to help fix the fixation elements 116 within the cardiac tissue. In other examples, the fixation elements 116 may include other structures such as barbs, spikes, tines (e.g. see FIG. 1) or the like to facilitate engagement with the surrounding cardiac tissue.

Those skilled in the art will recognize that the present disclosure may be manifested in a variety of forms other than the specific examples described and contemplated herein. For instance, as described herein, various examples include one or more modules described as performing various functions. However, other examples may include additional modules that split the described functions up over more modules than that described herein. Additionally, other examples may consolidate the described functions into fewer modules. Accordingly, departure in form and detail may be made without departing from the scope and spirit of the present disclosure as described in the appended claims.

What is claimed is:

1. An implantable medical device comprising:
a housing including a first end and a second end;
a fixation element disposed adjacent the first end of the housing;
a retrieval element disposed adjacent the second end of the housing;
the housing including an outer housing surface, the outer housing surface including a first region having a first surface texture with a first average surface roughness and a second region having a second surface texture with a second average surface roughness that is different from the first average surface roughness; and
an insulative layer disposed over the first surface texture and the second surface texture of the outer housing surface, wherein the insulative layer includes a first region overlying the first surface texture and a second region overlying the second surface texture, wherein an outer surface of the insulative layer emulates the first surface texture in the first region of the insulative layer and emulates the second surface texture in the second region of the insulative layer.

2. The implantable medical device of claim 1, wherein the implantable medical device is a leadless cardiac pacemaker.

3. The implantable medical device of claim 1, wherein the retrieval element is configured to be ensnared for subsequent removal of the implantable medical device.

4. The implantable medical device of claim 1, wherein the first surface texture with the first average surface roughness represents a native surface texture of the material forming the outer housing surface.

5. The implantable medical device of claim 4, wherein the second surface texture corresponds to a region of the outer housing surface that has been treated to make the second region of the outer housing surface smoother than the first region of the outer housing surface.

6. The implantable medical device of claim 1, wherein the first region of the outer housing surface comprises two or more distinct areas having the first surface texture.

7. The implantable medical device of claim 6, wherein the second region of the outer housing surface comprises two or more distinct areas having the second surface texture.

* * * * *